(12) United States Patent
Jiang et al.

(10) Patent No.: US 9,771,340 B2
(45) Date of Patent: *Sep. 26, 2017

(54) 2-AMINOTHIAZOLE DERIVATIVES AND METHODS OF PREPARING AND USING THE SAME

(71) Applicants: Huazhong University of Science & Technology, Wuhan (CN); Hangzhou Zhongmei Huadong Pharmaceutical Co., Ltd., Hangzhou (CN)

(72) Inventors: Fengchao Jiang, Wuhan (CN); Ping Zhou, Wuhan (CN); Jianguo Chen, Wuhan (CN); Yue Wang, Wuhan (CN); Baoshuai Cao, Wuhan (CN); Jia Yan, Wuhan (CN)

(73) Assignee: WUHAN INNAMUNE PHARMACEUTICAL CO., LTD., Wuhan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/016,126

(22) Filed: Sep. 1, 2013

(65) Prior Publication Data

US 2014/0004155 A1 Jan. 2, 2014

Related U.S. Application Data

(63) Continuation-in-part of application No. PCT/CN2012/070811, filed on Feb. 1, 2012.

(30) Foreign Application Priority Data

Mar. 2, 2011 (CN) .......................... 2011 1 0049687

(51) Int. Cl.
C07D 277/42 (2006.01)
C07D 277/46 (2006.01)
C07D 295/14 (2006.01)
C07D 417/12 (2006.01)

(52) U.S. Cl.
CPC .......... C07D 277/42 (2013.01); C07D 277/46 (2013.01); C07D 295/14 (2013.01); C07D 417/12 (2013.01)

(58) Field of Classification Search
CPC ... C07D 277/42; C07D 277/46; C07D 295/14
USPC ........................................................ 544/367
See application file for complete search history.

(56) References Cited

U.S. PATENT DOCUMENTS 3,957,766 A 5/1976 Berger et al.
2014/0073648 A1* 3/2014 Zhou .................... A61K 31/496
514/254.02

FOREIGN PATENT DOCUMENTS

| EP | 1486490 A1 | 12/2004 |
| WO | 9300342 A1 | 1/1993 |
| WO | WO-93/00342 A1 * | 1/1993 |
| WO | 9637493 A1 | 11/1996 |
| WO | 2007110337 A1 | 10/2007 |

OTHER PUBLICATIONS

Chemical Abstracts Registry No. 1333465-89-6, indexed in the Registry file on STN CAS Online Sep. 28, 2011.*
PubChem CID 7647607, created Jul. 30, 2006.*
Chemical Abstracts Registry No. 879615-95-9, indexed in the Registry file on STN CAS Online Apr. 7, 2006.*
Chemical Abstracts Registry No. 831179-04-5, indexed in the Registry file on STN CAS Online Feb. 15, 2005.*
Chemical Abstracts Registry No. 498537-38-5, indexed in the Registry file on STN CAS Online Mar. 13, 2003.*
Hassan et al., Bioorganic & Medicinal Chemistry Letters, 22(20), available online Sep. 3, 2012, pp. 6318-6323.*
El-Messery et al., European Journal of Medicinal Chemistry, 54, available online Jun. 18, 2012, pp. 615-625.*
Sélim et al., Bulletin de la Societe Chimique de France, 1968, No. 5, pp. 2117-2120.*
An English translation of Sélim et al., Bulletin de la Societe Chimique de France, 1968, No. 5, pp. 2117-2120.*
Papadopoulou et al., Synthesis and biological evaluation of new thiazolyl/benzothiazolyl-amides, derivatives of 4-phenyl-piperazine, II Farmaco, 2005, pp. 969-973, vol. 60, Editions Scientifiques et Medicales, IT.
Landreau et al., 2-Amino-4-dimethylamino-I-thia-3-azabutadienes as Precursors of Thiazoles, Phosphorus, Sulfur and Silicon and the related elements, 2002, pp. 2651-2659, vol. 177, Taylor and francis group, New York, US.

* cited by examiner

*Primary Examiner* — Laura L. Stockton
(74) *Attorney, Agent, or Firm* — Matthias Scholl, PC; Matthias Scholl

(57) ABSTRACT

2-aminothiazole derivatives represented by formula (I), where $R_1$ and $R_2$ represent cycloalkyls, respectively; or $R_1$ represents a substituted aromatic group, and $R_2$ represents H, a $C_1$-$C_{11}$ alkyl, —$CH_2Ph$ (benzyl), or a methyl ether including a $C_1$-$C_{11}$ alkyl. $R_3$ is a substituent including an amino group. X represents a carbonyl or a methylene and n is an integer from 0 to 5.

1 Claim, 11 Drawing Sheets

2-AMINOTHIAZOLE DERIVATIVES AND METHODS OF PREPARING AND USING THE SAME

CROSS-REFERENCE TO RELATED APPLICATIONS

This application is a continuation-in-part of International Patent Application No. PCT/CN2012/070811 with an international filing date of Feb. 1, 2012, designating the United States, now pending, and further claims priority benefits to Chinese Patent Application No. 201110049687.4 filed Mar. 2, 2011. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 14781 Memorial Drive, Suite 1319, Houston, Tex. 77079.

BACKGROUND OF THE INVENTION

Field of the Invention

The invention relates to a 2-aminothiazole derivative represented by formula (I),

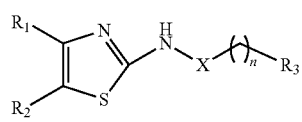

a preparation method thereof, and a method for using the same for the treatment of Alzheimer's disease (AD) by inhibiting acetylcholine esterase to inhibit apoptosis of nerve cells resulting from oxidative stresses, as well as a method for using the same for the treatment of anti-transplant rejection, anti-autoimmune disease, anti-ischemia-reperfusion injury, anti-chronic inflammation, and anti-endotoxaemia by inhibiting myeloid differential protein (MYD-88) to produce an immunosuppressive effect.

Description of the Related Art

Compounds containing 2-aminothiazole ring have been widely applied in anti-bacteria, anti-inflammation, and anti-allergy, and have been found in medicines of dopamine agonists, angiotensin receptor antagonists, and the like. However, applications of the compounds containing 2-aminothiazole ring in neurodegenerative diseases and kin immunosuppressant have been rarely reported.

AD is a neurodegenerative disorder based on the degeneration of primary neurons. Besides exceeding 7% of patients of 60 years of age and older have been tortured by AD, younger people trend to get AD. Thus, it has been a research hotspot in medical filed to develop an effective medicine for curing AD and other neurodegenerative disorders.

A plurality of factors account for the AD. Low activity of choline acetyltransferase and low Choline uptake capacity results in dysfunction of neurite transfer and that neurons or glial cells are incapable of providing sufficient nutrients, thereby leading to functional degradation of subcutaneous neuron system. Overactivity of glutamate receptor, high level of reactive oxygen (oxidative stresses), inflammation, and virus infection result in impaired metabolic pathways, and lowered energy production in mitochondria. In the presence of β-secretase and γ-secretase, β-amyloid precursor protein (APP) is transformed into β-amyloid (Aβ), which leads to amyloid agglomeration. Abnormal phosphorylation of Tau protein leads to tangles of nerve fibers and DNA and RNA mutations in nucleus or mitochondria.

Currently, the treatment of the AD is based on the control of the cause of disease and the symptom, including: improving the cognitive ability of patients, and weakening the functional degradation of subcutaneous neuron system. For example, using cholinoceptor agonists or acetylcholinesterase inhibitors (such as Aricept, Tacrine, and Donepezil) to increase the acetylcholine in vivo to improve the cognitive ability; and using medicines like calcium antagonist Nimodipine that is capable of lowering the free radicals (such as VE and Selegiline) and avoiding intracellular calcium overload to weaken the degradation of the neurons and the synapses. These means have some improvement during the treatment of early AD. However, neither acetylcholinesterase inhibitors nor other medicines have ideal clinical effects.

Although a plurality of regulatory factors induce neuronal apoptosis, principals of medicines for inhibiting of rapid degradation of nerve cells focus on either removing cell apoptosis signals to inhibit the initiation of cell apoptosis, or inhibiting cascade reaction after the initiation of the cell apoptosis. Non-histone chromosomal proteins poly (ADP-ribose) poly-merase (PARP) existing in eucaryotic cells are capable of regulating cellular process including DNA repair and maintenance of genomic stability, regulatory of transcription to regulating protein expression levels, and influence on replication and differentiation. The inhibition of PARP is capable of not only decreasing the impact on organs from inflammation, but also lowering the neural excitotoxicity of NMDA and KA. Thus, the inhibition of PARP protects the never cells, thereby being widely concerned in treatment of neurodegenerative diseases, nerve inflammation, and cerebral ischemia.

AD is a kind of multi-factorial diseases, and cannot be cured by single-targeted medicines. A combination of drugs is used in treatment, and advantages of multi-targeted drugs have been concerned. So far, inhibitors, such as ladostigil and rivastigmine, which can simultaneously act on Ache and brain MAO inhibitors, have been designed in accordance with the principal of the drug combination.

Besides, endogenous and exogenous risk factors stimulate each TLR of the innate immune system, stimulate signal transfer by key molecule myeloid differentiation protein 88 (MyD88), and activate NF-B and corresponding immune responses. Thus, MyD88 is a key molecule for the innate immune system. To inhibit the My88 is to inhibit the main reaction in the innate immune system and to achieve corresponding immunosuppressive effect. Because MyD88 is a new immunosuppressive target itself and available MyD88 inhibitors are mainly peptidomimetic compound or small molecules of complex structure, the preparation of MyD88 inhibitors are difficult and have high production cost, thereby being difficult to popularize in clinical treatment.

SUMMARY OF THE INVENTION

In view of the above-described problems, it is one objective of the invention to provide a 2-aminothiazole derivative, a preparation method thereof, and a method for using the same.

The 2-aminothiazole derivative of the invention represented by the formula (I) has an obvious effect on the acetylcholine esterase and PARP-1 related to Alzheimer's disease (AD), a simulated and predicted activity thereof exceeds that of the clinical drugs. Besides, the 2-aminothiazole derivative of the invention has effects on two targets simultaneously, thereby being applicable in the treatment of AD. Meanwhile, the aminothiazole derivative represented by the formula (I) is capable of matching with key active sites of MyD88 molecule to form a specific binding, thereby inhibiting the signal transfer of the MyD88. The aminothiazole derivative can be applied in treatment of anti-transplant rejection, anti-autoimmune disease, anti-ischemia-reperfusion injury, anti-chronic inflammation, and anti-endotoxaemia. The invention pioneered the application of such small molecules, and found a new medicine to cure the innate immunity disorders.

To achieve the above objective, in accordance with one embodiment of the invention, there is provided a 2-aminothiazole derivative.

The invention still provides a method for preparing the 2-aminothiazole derivative and intermediates related thereto.

The invention further provides use of the 2-aminothiazole derivative in inhibiting acetylcholine esterase and PARP-1 for treatment of related diseases, for example, AD, and other neurodegenerative diseases.

The invention further provides use of the 2-aminothiazole derivative in inhibition of myeloid differentiation protein (MyD-88) to produce an immunosuppression effect in treatment of anti-transplant rejection, anti-autoimmune disease, anti-ischemia-reperfusion injury, anti-chronic inflammation, and anti-endotoxaemia.

The 2-aminothiazole derivative is represented by the formula (I):

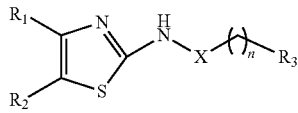

wherein $R_1$ represents a substituted aromatic group, and $R_2$ represents H; or $R_1$ and $R_2$ represent $—CH_2(CH_2)_2CH_2—$; $R_3$ is a substituent comprising amino; X represents a carbonyl

or a methylene

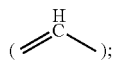

n is an integer from 0 to 5.

The preparation of the 2-aminothiazole derivative is based on syntheses of an intermediate (1), intermediate (2), and intermediate (3). The preparation method comprises the following steps: substituting hydroxyl radicals of diethanolamine by a halogen to yield bis(2-dichloroethyl) amine hydrochloride; allowing bis(2-dichloroethyl) amine hydrochloride and a substituted aromatic amine to react in the presence of microwave or in general reaction conditions to yield a substituted aromatic piperazine (intermediate (1)); heating a substituted methyl aromatic ketone and a substituted thiourea in the presence of iodine molecules to perform reaction to yield a 2-aminothiazole derivative (intermediate (2)); substituting the 2-aminothiazole derivative (the intermediate (2)) by a halogenated acyl halide to yield a co-halogenated amide derivative (intermediate (3)); and acquiring target compounds by alkylation reaction of corresponding intermediates. For example, allowing the intermediate (1) to react with the intermediate (3) to yield the 2-aminothiazole derivative comprising a heterocycle; or allowing the intermediate (3) to react with a benzylamine to yield a product, and allowing the product to react with a corresponding halohydrocarbon to yield the 2-aminothiazole derivative comprising a general amino; or performing a condensation reaction between the intermediate (2) and a substituted aldehyde compound catalyzed by an alkali to yield the 2-aminothiazole derivative comprising methylene.

1. Synthesis of the Intermediates

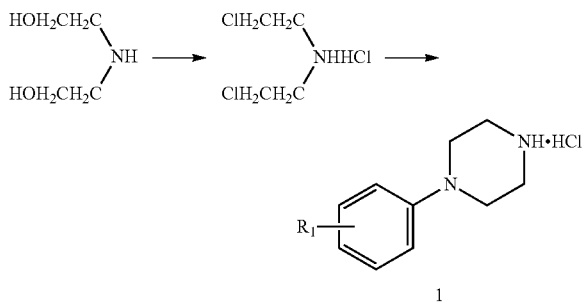

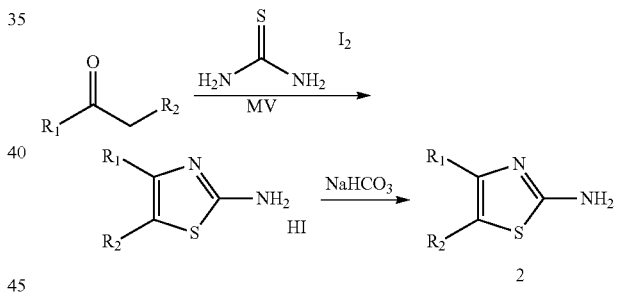

2. Synthesis of Target Compounds

If X represents a carbonyl, methods for synthesizing corresponding target compounds are as follows:

Method 1

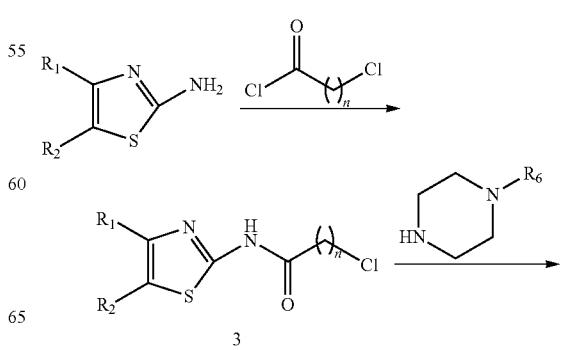

-continued

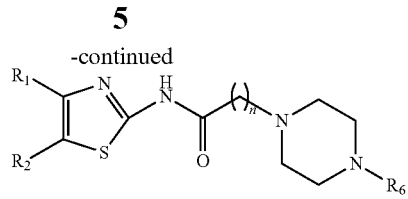

Method 2

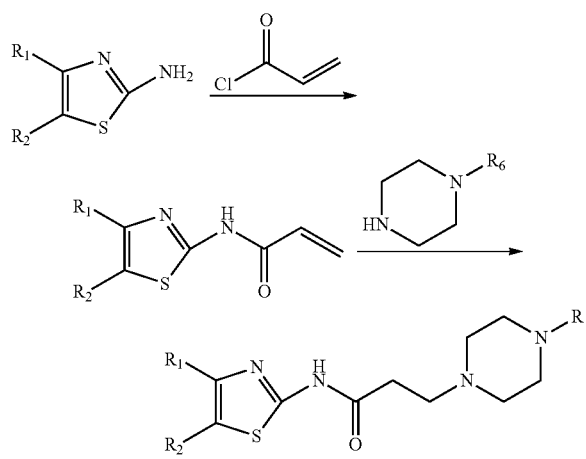

Method 3

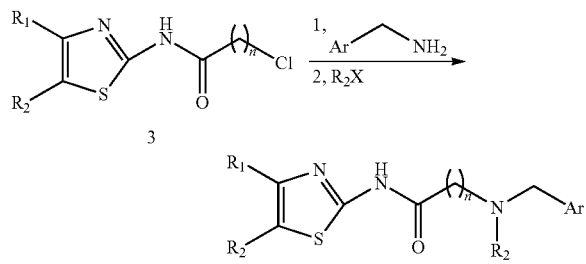

Method 4

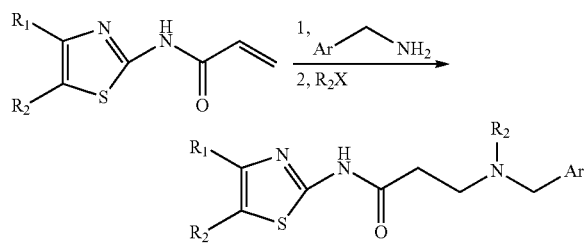

If X represents a methylene, a method for synthesizing corresponding target compounds are as follows:

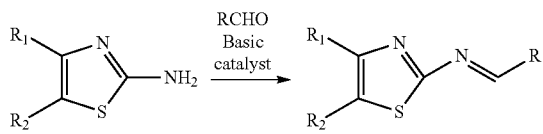

Furthermore, the invention is based on using the PARP1 receptor, AchE and MyD88 receptors as targets, so that the compound of the invention has effect on diseases caused by target points related to PARP1 receptor, AchE, and MyD88 receptors.

The 2-aminothiazole derivative represented by the formula (I) has an appropriate molecular weight and stable structure, and is capable of penetrating the cell membrane. The expected side effect of the 2-aminothiazole derivative is small.

The 2-aminothiazole derivative represented by the formula (I) is used as an acetylcholinesterase inhibitor in treatment of early AD and other neurodegenerative diseases.

The 2-aminothiazole derivative represented by the formula (I) is used as a nerve cell protecting agent in treatment of diseases related to neuronal apoptosis induced by factors comprising oxidative stress.

The 2-aminothiazole derivative represented by the formula (I) is used as a MyD88 inhibitor to reduce rejections after organ transplantation.

The 2-aminothiazole derivative represented by the formula (I) is used as an immunomodulator for treatment of autoimmune diseases and chronic inflammatory diseases.

The 2-aminothiazole derivative represented by the formula (I) is used as an immunomodulator for treatment of ischemia-reperfusion injuries.

Advantages of the invention are as follows: the invention has devised a group of the 2-aminothiazole derivatives represented by the formula (I) that have been proved to have effects on the inhibition of acetylcholine esterase and the PARP-1 and on the protection of apoptosis of nerve cells resulting from oxidative stresses, so that the 2-aminothiazole derivatives represented by the formula (I) are probable to become an effective medicine in the treatment of early Alzheimer's disease (AD). Experiments of the 2-aminothiazole derivatives used as the specific inhibitor of MyD88 have proved that the 2-aminothiazole derivatives of the invention have obvious effect in treatment of rejection after organ transplantation, induction of immune tolerance, the treatment of various inflammatory responses, and the prevention of ischemia-reperfusion injury.

The 2-aminothiazole derivatives of the invention have stable structures and good anti-oxidative properties, and are beneficial for improvements of the pharmacological activity and pharmacokinetic characteristics. Compared with conventional acetylcholine esterase inhibitors, PARP-1 inhibitors, and MyD88 inhibitors, preparation of the 2-aminothiazole derivatives of the invention uses raw materials of low cost, such as, diethanolamine, iodine molecules, aromatic ketones, and thiourea, simple steps, and products being simple in separation and purification.

BRIEF DESCRIPTION OF THE DRAWINGS

Specifically, FIG. 1 is a block diagram of test results of inhibition effect of aminothiazole derivative provided in the invention on acetylcholine esterase (AchE); the AchE was collected from SD rats;

FIG. 2 is a block diagram of test results of inhibition effect of aminothiazole derivative (a concentration of 1 μM) provided in the invention on Poly ADP-ribose polymerase-1 (PARP-1);

FIG. 3 is a block diagram of cytoprotective ability of aminothiazole derivatives provided in the invention against neuronal apoptosis induced by oxidative stress of hydrogen peroxide ($H_2O_2$); cells are dopaminergic neuroblastoma tumor cells SH-SY5Y from human body;

FIG. 4 is a block diagram of cytoprotective ability of aminothiazole derivatives provided in the invention against neuronal apoptosis resulting from cobalt chloride ($CoCl_2$)-induced hypoxic injury; cells are dopaminergic neuroblastoma tumor cells SH-SY5Y from human body;

FIG. 5 is a picture of human dopaminergic neuroblastoma tumor SH-SY5Y cells after being damaged by cobalt chloride ($CoCl_2$)-induced hypoxic injury;

FIG. 6 is a picture showing cobalt chloride ($CoCl_2$)-induced hypoxic injury-damaged human dopaminergic neuroblastoma tumor SH-SY5Y cells being added with aminothiazole derivatives provided in the invention;

FIG. 7 shows a relationship between a dose of aminothiazole derivatives and inhibition on T cell activation;

FIG. 8 shows a relationship between a dose of aminothiazole derivatives and inhibition on expression of CD80; LPS, CPG, myocardial tissue homogenized solvent stimulating DC;

FIG. 9 shows a relationship between a dose of aminothiazole derivatives and inhibition on expression of DC surface CD80;

FIG. 10 shows a relationship between a dose of aminothiazole derivatives and inhibition on expression of macrophage surface CD80; and FIG. 11 shows experimental groups administered by aminothiazole derivatives: MyD88KO NOD mice, MyD88KO/+NOD mice, and NOD mice.

DETAILED DESCRIPTION OF THE EMBODIMENTS

Figure 1:
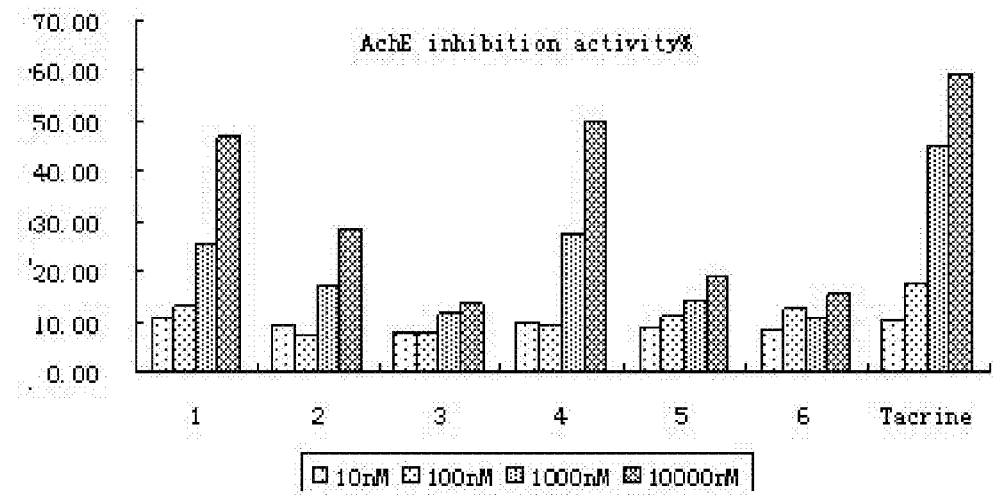
FIG. 1 shows inhibition effect of an aminothiazole derivative in accordance with one embodiment of the invention on AchE.

For further illustrating the invention, experiments detailing a 2-aminothiazole derivative, a preparation method thereof, and a method for using the same are described below. It should be noted that the following examples are intended to describe and not to limit the invention.

1. Compounds

A 2-aminothiazole derivative disclosed in the invention is represented by formula (I)

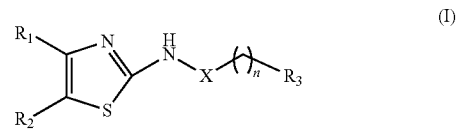

wherein $R_1$ and $R_2$ represent a cycloalkyl, respectively; or $R_1$ represents a substituted aromatic group, and $R_2$ represents H, a $C_1$-$C_{11}$ alkyl, —$CH_2$Ph (benzyl), or a methyl ether (—$CH_2$OR) comprising a $C_1$-$C_{11}$ alkyl; $R_3$ is a group comprising amino; X represents a carbonyl

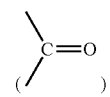

or a methylene

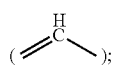

and n=0-5.

Specifically, $R_1$ and $R_2$ comprise cyclic hydrocarbons comprising between 3 and 7 rings; or when $R_2$ is an alkyl (comprising H, —$CH_3$, —$C_2H_5$, —$CH_2$Ph (benzyl), and —$CH_2$OR), the substituted aromatic group represented by $R_1$ is a substituted benzene ring (a), a substituted pyridine (b), a substituted pyrrole (c), a substituted indole (d), or a substituted imidazole (e):

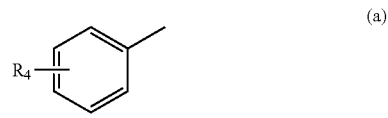

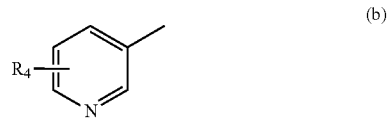

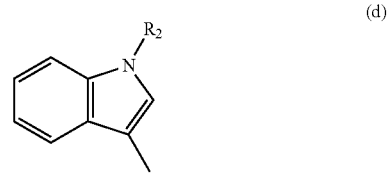

wherein $R_4$ represents a $C_1$-$C_{11}$ hydrocarbon alkyl, a cyclic hydrocarbon comprising between 3 and 7 rings, an alkoxy comprising a $C_1$-$C_{10}$ alkyl, a carboxylate group comprising a $C_1$-$C_{10}$ alkyl, or a halogen group (—Cl, —Br, and —CN).

A substituted position of $R_4$ is a para-position, an ortho-position, or a meta-position.

When X in formula (I) represents the carbonyl, the group comprising amino ($R_3$) is a piperazine derivative (f), a piperidine derivative (g), an apyrrolidine derivative (h), a pyridine (i), or an amino derivative (j):

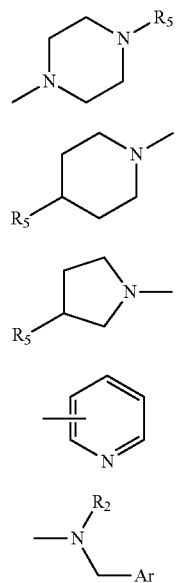

wherein $R_5$ represents a substituted benzene ring (a), a substituted pyridine (b), or a substituted pyrrole (c);

Ar is -benzyl or 3-pyridylmethyl.

When X in formula (I) represents the methylene, the group comprising amino ($R_3$) is a pyridine (i), 3-indole, or 4-imidazole; and n=0.

2. Synthesis Of Compounds

The synthesis of the 2-aminothiazole derivative represented by formula (I) comprises the synthesis of intermediates and the target compounds.

Synthesis of Intermediates

Preparation of a substituted phenylpiperazine (an intermediate (1)) comprises substituting hydroxyl radicals of diethanolamine by a halogen to yield bis (2-dichloroethyl) amine hydrochloride; and performing cyclization between bis (2-dichloroethyl) amine hydrochloride and a substituted aromatic amine to yield substituted phenylpiperazine. The preparation employs microwave catalytic synthesis or conventional synthesis.

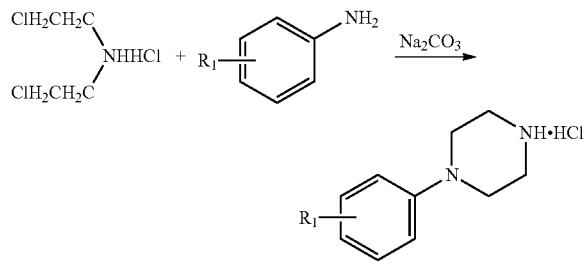

1) microwave catalytic synthesis comprises: adding bis (2-dichloroethyl) amine hydrochloride and a substituted aniline (at a molar ratio of 1:1.2) to n-butanol to form a mixture, evenly stirring the mixture, treating the mixture by microwave radiation at a power of 195 w for between 2 and 8 min, cooling the mixture and adding a certain amount of powdered anhydrous sodium carbonate, continuing microwave radiation for 15-20 min, filtrating a hot mixture, standing a filtrate for allowing the substituted phenylpiperazine to precipitate.

2) conventional synthesis: adding bis(2-dichloroethyl) amine hydrochloride to n-butanol to form a mixture, stirring the mixture while adding a substituted aniline (a molar ratio between the substituted aniline and the bis(2-dichloroethyl) amine hydrochloride is 1:1.2), heating, refluxing, and stirring for performing reaction for between 20 and 60 h, cooling a resulting mixture and adding a certain amount of powdered anhydrous sodium carbonate, continuing refluxing and stirring for reaction for between 48 and 150 h, using a TLC monitor for ensuring a completed reaction. Subsequent treatment is the same as the former.

Preparation of a 4,5-substituted-2-aminothiazole (an intermediate (2)) comprises: heating a substituted methyl aromatic ketone and a substituted thiourea in the presence of iodine molecules to perform reaction to yield the 4,5-substitued-2-aminothiazole. The preparation employs microwave catalytic synthesis or conventional synthesis.

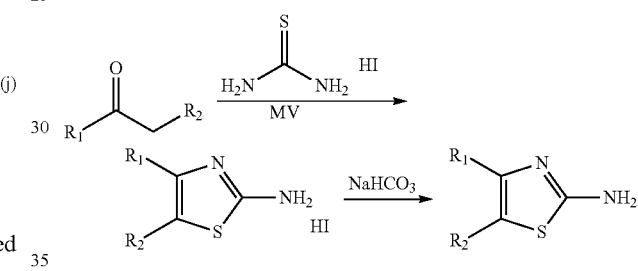

Evenly mixing powdered thiourea and iodine at a molar ratio of 2:1 to form a mixture, adding a substituted ketone derivative to the mixture while stirring; allowing a resulting mixture to react for several minutes in presence of microwave and a proper power; adding a small amount of ether to a reacted mixture, filtrating, washing a precipitation by ether to yield a hydroiodide of 2-aminothiazole; dissolving the hydroiodide of 2-aminothiazole in hot water, adding a calculated amount of solid sodium bicarbonate while stirring to yield a mixed solution, neutralizing the pH value of the mixed solution; filtrating the mixed solution; washing a precipitation by water; and desiccating a product to yield a crude 2-aminothiazole.

Preparation of a 4,5-substitued-2-aminothiazole-ω-halogenatedamide (an intermediate (3)) comprises: substituting the 4,5-substitued-2-aminothiazole by a halogenated acyl halide to yield the 4,5-substitued-2-aminothiazole-ω-halogenated amide.

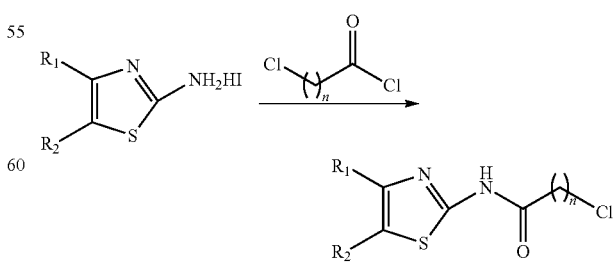

adding the 4,5-substitued-2-aminothiazole in an anhydrous THF, dropping the halogenated acyl halide (such as chloroacetyl chloride, a molar ratio between the halogenated acyl halide and the 4,5-substitued-2-aminothiazole), stirring a resulting mixture at room temperature for reaction, monitoring the reaction by TLC until the reaction is completed; and separating the sample by chromatography.

Chloroacetyl chloride can be replaced by acryloyl chloride to produce a corresponding 4,5-substitued-2-aminothiazole-N-chloropropionamide Synthesis of Target Compounds Preparation of 2-(4-substituted piperazin-1-yl)-N-4,5-disubstituted thiazole-2-acetamide (Method 1) comprises: performing alkylation reaction between the 4,5-substitued-2-aminothiazole-ω-halogenated amide (the intermediate 3) and the substituted piperazine hydrochloride (the intermediate (1)) to yield a target compound comprising heterocycle (I).

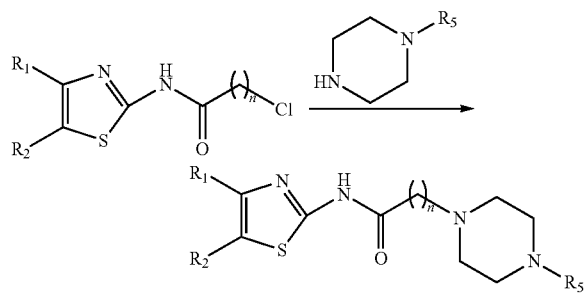

Dissolving the 4,5-substitued-2-aminothiazole-ω-halogenated amide (the intermediate 3) and the substituted piperazine hydrochloride (the intermediate (1)) of equivalent molar in dimethyl formamide (DMF), adding a carbonate or an organic base and a corresponding catalyst in DMF to form a mixture; allowing the mixture to react at a temperature of between 50 and 100° C., monitoring the reaction by TLC until the reaction is completed; adding water to a resulting solution for treatment, abstracting an organic phase by an organic solvent; washing the organic phase by water, desiccating, and separating the organic phase by chromatography.

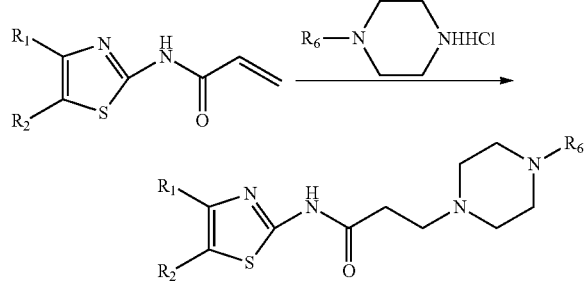

Preparation of 3-(4-substituted piperazin-1-yl)-N-4,5-substituted thiazole-2-propanamide (method 2)

Adding 4,5-substituted 2-aminothiazol-N-acrylamide and the substituted piperazine hydrochloride (the intermediate (1)) of equivalent molar in a related solvent, adding an organic base, and allowing a mixture to react at a temperature of between 50 and 100° C., monitoring the reaction by TLC until the reaction is completed; adding water to a resulting solution for treatment, abstracting an organic phase by an organic solvent; washing the organic phase by water, desiccating, and separating the organic phase by chromatography.

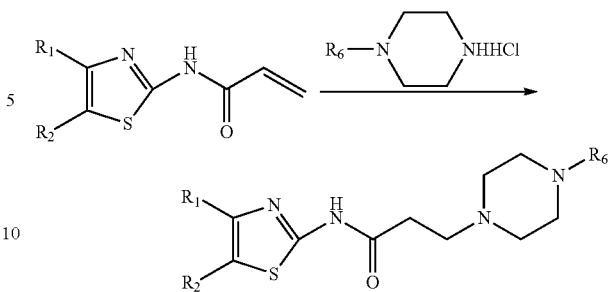

Preparation of 3-(N,N-substituted amino)-N-4,5-substituted thiazol-2-amide (method 3) comprises: Performing reaction between the 4,5-substitued-2-aminothiazole-ω-halogenated amide and a 2-aminomethyl derivative, allowing a product to react with a corresponding halohydrocarbon to yield a target compound comprising general amino. Or performing addition reaction between 4,5-substituted 2-aminothiazol-N-acrylamide and the 2-aminomethyl derivative, substituting a product by a halohydrocarbon to yield 3-(N,N-substituted amino)-N-4,5-substituted thiazol-2-propionamide.

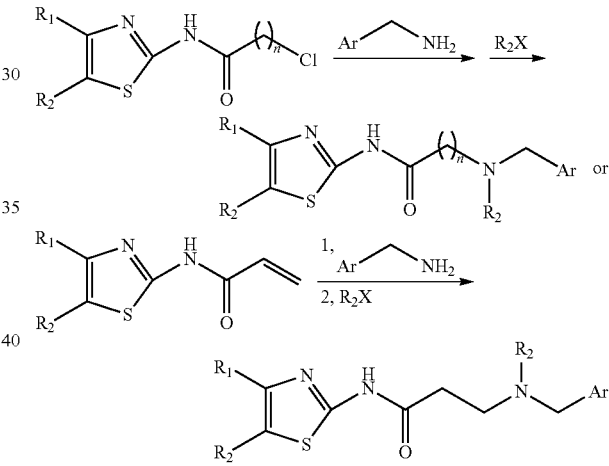

dissolving 4,5-substitued-2-aminothiazole-ω-halogenated amide (the intermediate (3)) and the 2-aminomethyl derivative of equivalent molar to a related solvent, adding an organic base, allowing a mixture to react at a temperature of between 50 and 100° C., monitoring the reaction by TLC until the reaction is completed; evaporating the solvent in a reduced pressure, adding DMF, and equivalent molar of the halohydrocarbon and corresponding alkali to the mixture; stirring a resulting mixture for performing reaction at the temperature between 50 and 100° C., monitoring the reaction by TLC until the reaction is completed (between 4 and 10 h); adding water to a resulting solution for treatment, abstracting an organic phase by an organic solvent; washing the organic phase by water, desiccating, and separating the organic phase by chromatography.

Preparation of an aminothiazole derivative (II) (method 4) comprises: performing condensation reaction between 4,5-substitued-2-aminothiazole (the intermediate (2)) and a substitued methanol catalyzed by an organic base to yield the aminothiazole derivative (II). The preparation employs microwave catalytic synthesis or conventional synthesis.

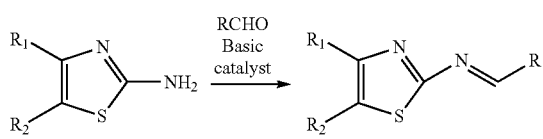

3. Treatment Schemes and Methods

In treatment, the aminothiazole derivatives (I) are provided to patients by any proper means, such as direct administration (local administration, such as injection, transplantation, or locally applied on objective tissues) and systemic administration (by injection administration and oral administration). By means of intravenous injection, subcutaneous injection, intramolecular administration, intraocular administration, celiac administration, intramuscular injection, oral administration, intradermal injection, transdermal administration, endotracheal administration, intracerebral administration, intracranial administration, intraspinal administration, intraventricular administration, intrathecal administration, intracisternal administration, intracapsular administration, and inhalation, compounds are administered to special parts by parenteral routes, thereby being capable of combing with part of aqueous or physiologically compatible liquid suspension and water solution.

The 2-aminothiazole derivative (I) of the invention can be applied in treatment of some neurodegenerative diseases, for example, early Alzheimer's disease (AD), diseases related to rapid apoptosis of nerve cells caused by oxidative stress, autoimmune diseases and chronic inflammatory diseases, ischemia-reperfusion injury diseases, and in treatment of reducing rejection after transplantation and Transplantation tolerance induction and maintenance. The medicine is one-time administered or continuously administered. The new compound can be individually administered or combined with other reagents. For example, compound in compound therapy. The new medicine contains a certain amount of the effective new compound. The amount of the new compound is adjusted according to the state of an illness. The weight of the patient, severity of the disease, the administration means, and pharmacist compounding drugs from prescribed ingredients, are all taken into consideration in compounding the medicines.

The 2-aminothiazole derivative (I) of the invention can be continuously or intermittently administered in the form of proper drug molecules by any means. The oral administration and intraperitoneal administration are proper administration means.

4. Examples

EXAMPLE 1

Preparation of 4-phenyl-2-aminothiazole 7.6 g (0.1 mol) of thiourea, 12.7 g (0.05 mol) of iodine were ground and evenly mixed; 6.0 g (0.05 mol) of acetophenone were added and evenly stirred to form a mixture; the mixture was allowed to reaction for between 2 and 3 min in a microwave reactor at a power of between 150 and 200 W. After the reaction, between 40 and 50 mL of ether was added. A resulting mixture was stirred and filtrated to yield a filter cake. The filter cake was then washed by a small amount of ether for several times to yield a first pale yellow solid. The first pale yellow solid was dissolved in 150 mL of water at a temperature of 80° C. to yield a solution. The solution was stirred while adding solid sodium bicarbonate solid. pH value was controlled between 7 and 8. The solution was suction filtrated, after several times of washing by water, 5.5 g (0.031 mol) of a second pale yellow solid was obtained, a crude yield was 62.5%. The second pale yellow solid was re-crystallized by anhydrous ethanol to yield 3.4 g (0.019 mol) of a third pale yellow needle-like crystal having a melting point (mp) of between 153 and 156° C. IR (KBr, σ/cm$^{-1}$) 3435 (s), 3253 (m, ν-NH$_2$); 3113.55 (m, thiazole ring ν-HC=); 1599 (s, ν-C=N); 1517 (s, Benz ring skelecton); 1338 (m, νC—N); 768.8 (thiazole ring skelecton); 716 (δBenz ring bend.); $^1$H NMR (CDCl$_3$, 300 MHz, δ/ppm) 7.78 (d, J=8 Hz, 2H, Aryl-H), 7.47 (t, J=27 Hz, 2H), 7.28 (t, J=15 Hz, 1H, Aryl-H), 6.73 (s, 1H, thiazole-H), 5.11 (s, 2H, —NH$_2$).

EXAMPLE 2

Preparation of 1-(4-methoxyphenyl) piperazine

Synthesis of bis(2-dichloro ethyl) amine nicotinate:

1) A first mixed solution was prepared by diluting diethanolamine using chloroform. A second mixed solution was prepared by mixing chlorinated sulfoxid with chloroform. The first mixed solution was dropped to the second mixed solution while stirring after the second mixed solution was cooled to a temperature approximately 0° C., a molar ratio between chlorinated sulfoxid and diethanolamine was controlled at 1:4. Thereafter, a resulting mixture was stirring for reaction for between 2 and 5 h. The temperature was then increased to between 30 and 70° C. for allowing the mixture to react at the temperature therein for 2 h. After the reaction, anhydrous ethanol was added. The mixture was then cooled and suction filtrated to obtain a solid. The solid was then washed by ethanol and ether, respectively, and desiccated to obtain bis(2-dichloro ethyl) amine nicotinate having a yield of 97.8% and an mp of 205.1-207.0° C.

2) 4.3 g (24 mmol) of bis(2-dichloro ethyl) amine nicotinate and 2.5 g (20 mmol) of 4-methoxyaniline solid were added to 50 mL of n-butanol and stirred evenly to form a mixture. The mixture was then treated by microwave irradiation at a power of 195 W for 6 min, and cooled. 1.3 g (12 mmol) of anhydrous sodium carbonate powder was added, and a new mixture was treated by the microwave irradiation for another 19 min, and filtered to yield a filter cake. The filter cake was washed by a small amount of hot n-butanol. A filtrate was cooled to the room temperature, and evenly mixed with anhydrous ethanol of an equivalent volume. The filter cake was washed by anhydrous ethanol and ether, respectively, and re-crystallized by anhydrous ethanol/ether (1:2). A product was desiccated in vacuum to obtain 3.2 g of white crystals having a yield of 76.9% and an mp of 203.6-205.2° C. UV (λ/nm) λmax=246; HPLC (min) Rt=2.717; $^1$H-NMR (DMSO-6D, 300 MHz, δ/ppm) 7.03-6.89 (m, 4H, Aryl-H), 4.69 (s, 1H, N—H), 3.70 (s, 3H, CH3O), 3.32-3.32 (t, 4H, NCH$_2$), 3.25-3.22 (t, 4H, NCH$_2$); $^{13}$C-NMR (DMSO-6D, 300 MHz, δ/ppm) 154.6 (C8), 143.6 (C5), 119.8 (C6, 10), 114.9 (C7, 9), 55.6 (C11), 47.7 (C1, 4), 43.2 (C2, 3).

EXAMPLE 3

Preparation of 2-chloro-N-(4-phenylthiazol-2-yl) acetamide 3.5 g (0.02 mol) of 4-phenyl-2-aminothiazole was dissolved in a small amount of tetrahydrofuran to form a solution; 2.5 g (0.024 mol) of chloroacetyl chloride was dropped in an ice condition until the solution turned pale yellow. The solution was stirred at the room temperature for reaction for 4 h, and a TLC monitor was employed to monitor the reaction (ethyl acetate: petroleum ether-1:4, Rf: 0.2). After the reaction, a product and silica gel at a ratio of 1:15 was treated by silica gel column chromatography, a mobile phase was composed of ethyl acetate and petroleum ether at a ratio of 1:4. 1.8 g of yellow granular compound was obtained (7.14 mmol, yield of 35.7%, and an mp of 179-181° C.).

EXAMPLE 4

Preparation of 2-(4-(4-methoxyphenyl) piperazin-1-yl)-N-(4-phenyl-thiazol-2-yl) acetamide (labeled as TJ-M201005)

0.5 g (2.1 mmol) of 4-phenyl-thiazol-2-(2-chloro)-acetamide and 0.48 g (2.1 mmol) of 1-(4-methoxyphenyl) piperazine hydrochloride are dissolved in a 20 mL of DMF, 0.29 g (2.1 mmol) of potassium carbonate and a catalytic amount of potassium iodide were added. A mixture was heated at a temperature of 80° C. for reaction for approximately 5 h, during which the reaction was monitored by TLC monitor. After the reaction, the reaction solution was added with a saturated brine for treatment, and was then extracted by dichloromethane for several times. A dichloromethane solution was combined, washed by the saturated brine, and was desiccated. After condensation, silica gel column chromatography was performed for abstraction by using a mobile phase comprising ethyl acetate and petroleum ether at a ratio of 1:10, 0.6 g (1.5 mmol) of Khaki yellow solid having a yield of 70% and an mp of 186-189° C. was obtained after condensation. UV (CH$_3$OH) A$_{max}$/nm 268.1, 231.0; $^1$H-NMR (CDCl$_3$): 2.83 (t, J=8.4 Hz, 4H), 3.22 (t, J=8.4 Hz, 4H), 3.35 (s, 2H), 3.80 (s, 3H), 6.87 (d, J=9.2 Hz, 2H), 6.95 (d, J=9.2 Hz), 7.18 (s, 1H), 7.27 (s, CDCl$_3$), 7.34 (d, J=8.0 Hz, 1H), 7.42 (t, J=8.0 Hz, 2H), 7.85 (d, J=8.0 Hz, 2H); $^{13}$C-NMR (CDCl$_3$) 50.85, 53.75, 55.58, 61.10, 107.87, 114.55, 118.66, 126.09, 128.07, 128.76, 134.34, 140.54, 147.35, 150.13, 157.02, 168.38.

EXAMPLE 5

Preparation of 2-(4-(4-methoxyphenyl) piperazin-1-yl)-N-(4-phenyl-thiazol-2-yl) butyramide (labeled as TJ-M201018)

0.6 g (2.1 mmol) of 4-phenyl-thiazol-2-(2-bromo)-butyramide and 0.48 g (2.1 mmol) of 1-(4-methoxyphenyl) piperazine hydrochloride were dissolved in 20 mL of DMF. 0.29 g (2.1 mmol) of potassium carbonate and a catalytic amount of potassium iodide were added. Reaction conditions were the same as that in Example 4. 0.7 g (1.5 mmol) of yellow crystals were obtained, a yield thereof was 73%, and a melting point thereof was 189-192° C. UV (CH$_3$OH) A$_{max}$/nm 262.0, 233.4; $^1$H-NMR (CDCl$_3$): 2.68 (m, 2H), 2.83-3.31 (t, J=5.4 Hz, 4H), 2.87 (m, 4H), 3.22 (t, J=8.4 Hz, 4H), 3.55 (s, 2H), 3.80 (s, 3H), 6.92 (d, J=9.2 Hz, 2H), 6.91 (d, J=5.4 Hz), 7.15 (s, 1H), 7.34 (d, J=8.0 Hz, 1H), 7.42 (t, J=8.0 Hz, 2H), 7.85 (d, J=8.0 Hz, 2H); $^{13}$C-NMR (CDCl$_3$), 28.45, 31.26, 50.85, 52.70, 55.59, 61.10, 107.29, 114.55, 118.60, 127.92, 128.97, 128.76, 134.34, 146.34, 149.35, 155.18, 157.42, 168.38, 206.98.

EXAMPLE 6

Preparation of 2-(4-(p-tolyl) piperazin-1-yl)-N-(4-phenyl-thiazol-2-yl)-acetamide (labeled as TJ-M201002)

Preparation method was the same as that in Example 5, a yield of the product was 82%, and a melting point thereof was 176478° C. UV (CH$_3$OH) A$_{max}$/nm 268.1, 235.1; $^1$H-NMR (CDCl$_3$) 2.30 (s, 3H), 2.81 (t, J=6.4 Hz, 4H), 3.26 (t, J=6.4 Hz, 4H), 3.34 (s, 2H) 6.88 (d, J=7.2 Hz, 2H), 7.11 (d, J=7.2 Hz, 2H) 7.18 (s, 1H) 7.27 (s, CDCl$_3$) 6.873-7.868 (m, 5H); $^{13}$C-NMR (CDCl$_3$) 20.45, 49.85, 53.72, 61.15, 107.86, 116.75, 126.09, 127.92, 128.60, 128.76, 129.75, 134.35, 148.78, 150.14, 157.02, 168.43.

EXAMPLE 7

Preparation of 3-(4-benzyl-piperazin-1-yl)-N-(4-phenyl-thiazol-2-yl)-propionamide (labeled as TJ-M201015)

0.5 g (2.2 mmol) 4-phenyl-thiazol-2-acrylamide, 0.24 g (2.2 mmol) of benzylpiperazine was dissolved in 30 mL of ethanol, 0.22 g (2.2 mmol) of triethylamine was added to form a mixture. The mixture was heated at a temperature of 60° C. while stirring for reaction, and the reaction was monitored by TLC (ethyl acetate: petroleum ether: triethylamine-1:4:1 d). After the reaction, a large amount of ethanol was removed by reducing pressure. Silica gel column chromatography comprising a mobile phase (ethyl acetate: petroleum ether/triethylamine-1:8/1%) was performed for purification. 0.5 g (1.2 mmol) of pale yellow granular compound was obtained. A yield thereof was 56.0%, and a melting point thereof of 197-201° C. UV (CH$_3$OH) A$_{max}$/nm 260.0, 225.0; $^1$H-NMR (CDCl$_3$) 2.62 (t, J=6.0 Hz, 2H), 2.70 (s, 8H), 2.79 (t, J=6.0 Hz, 2H), 3.63 (s, 2H), 7.15 (s, 1H), 7.27 (s, CDCl$_3$), 7.29-7.37 (m, 6H), 7.45 (t, 6.4 Hz, 2H), 7.90 (d, J=7.2 Hz, 2H); $^{13}$C-NMR (CDCl$_3$): 30.93, 31.17, 52.21, 52.98, 62.92, 107.28, 125.98, 127.26, 127.82, 128.33, 129.23, 134.61, 149.82, 157.48, 170.10, 206.97.

EXAMPLE 8

Preparation of 3-(4-(4-methoxyphenyl) piperazin-1-yl-N-(4-phenyl-thiazol-2-yl)-propionamide (labeled as TJ-M201021)

The preparation method was the same as that in Example 6. A mobile phase of column chromatography comprised ethyl acetate, petroleum ether, and triethylamine at a ratio of 1:4:1‰. 0.5 g (1.2 mmol) of white flaky crystals was obtained. A yield thereof was 53.9%, and a melting point thereof was 202-204° C. UV (CH$_3$OH) A$_{max}$/nm 261.0, 233.2; $^1$H-NMR (CDCl$_3$) 2.68 (m, 4H), 2.83-2.87 (m, 6H), 3.31 (t, J=4.8 Hz, 2H), 3.81 (s, 3H), 6.91 (d, J=5.2 Hz, 2H), 6.98 (d, J=5.2 Hz, 2H), 7.14 (s, 1H), 7.27 (s, CDCl$_3$) 7.73 (d, J=7.2 Hz, 1H), 7.38 (t, J=7.6 Hz, 2H), 7.85 (d, J=5.2 Hz, 2H); $^{13}$C-NMR (CDCl$_3$). 31.26, 50.80, 52.51, 53.06, 55.59, 107.28, 114.52, 118.62, 127.81, 128.62, 134.45, 145.32, 149.86, 154.17, 157.41, 169.99, 206.98.

EXAMPLE 9

Preparation of 3-(N,N-pyridylmethyl-ethyl amine)-N-(4-phenyl-thiazole-5-methyl-2-yl)-propionamide (labeled as TJ-M201041)

0.5 g (2.0 mmol) of 4-phenyl-5-methyl-thiazole-2-acrylamide and 0.22 g (2.0 mmol) of 2-(aminomethyl) pyridine were dissolved in 30 mL of anhydrous ethanol. 0.21 g (2.0 mmol) of triethylamine was added. A mixture was stirred at a temperature between 50 and 100° C. for reaction. The reaction was monitored by TLC (ethyl acetate: petroleum ether: triethylamine-1:3:1 d). After the reaction, a solvent was removed. 15 mL of DMF and 0.24 g (2.2 mmol) of bromoethane and a proper amount of potassium carbonate were added for allowing reaction at a temperature of between 50 and 100° C. The reaction was monitored by TLC (Ethyl acetate: petroleum ether: triethylamine-4:1:1 d). After the reaction, silica gel column chromatography comprising a mobile phase (ethyl acetate: petroleum ether: triethylamine-8:1:1%) was performed for purification. 0.41 g (1.0 mmol) of a white granular compound was obtained. A yield thereof was 50%, a melting point thereof was 185-187° C. UV (CH$_3$OH) A$_{max}$/nm 269.9, 230.0, $^1$H-NMR (CDCl$_3$) 1.22 (t, J=7.2 Hz, 3H), 2.64 (t, J=6.4 Hz, 2H), 2.76 (q, J=7.2 Hz, 2H), 2.89 (t, J=6.4 Hz, 2H), 3.25 (s, 3H), 3.78 (s, 2H), 7.27 (s, CDCl$_3$), 7.58 (d, J=7.2 Hz, 2H), 7.45 (t, J=7.8 Hz, 2H), 7.35 (t, J=7.8 Hz, 2H), 7.34 (m, 2H), 7.97 (d, J=7.2 Hz, 2H), $^{13}$C-NMR (CDCl$_3$) 10.36, 31.69, 45.87, 48.11, 58.05, 60.82, 107.13, 125.99, 127.69, 127.77, 128.63, 128.68, 129.48, 134.75, 149.87, 157.30, 170.11.

EXAMPLE 10

Preparation of N-2-isonicotinoyl-4-phenyl-thiazol-2-amine (labeled as TJ-M201050)

1 g (5.6 mmol) of 4-phenyl-2-aminothiazole (I), 1.02 g (8.4 mmol) of isonicotinic acid, 0.68 g (5.6 mmol) of DMAP, 1.73 g (5.6 mmol) of DCC were mixed with 15 mL acetone to form a mixture. The mixture was shook at a temperature of 25° C. for 24 h in a parallel synthesis device to obtain a white solid. The white solid was washed by acetone (3×3 mL). Acetone solutions were combined to yield a combined solution. Acetone was removed from the combined solution by reducing pressure to obtain a faint yellow solid. The faint yellow solid was washed, neutralized by distilled water, and suction filtrated to obtain a light yellow powder. The light yellow powder was re-crystallized by 75% ethanol and a product was dried in vacuum to obtain 0.9 g of light yellow needle-like crystals. A yield thereof was 60%, a melting point thereof was 213-216° C. UV (MeOH, λmax/nm): 228.; IR (KBrσ/cm$^{-1}$): 3400 (w, v$_{N—H}$), 3028 (w, v$_{Ar—H}$), 1602 (m, v$_{C=O}$), 1542 (s, thiazole ring v$_{—C=N}$), 704 (m, δBenz ring bend); $^1$H-NMR (CDCl$_3$, 300 MHz, δ/ppm): 7.25 (dd, 1H, Aryl-H), 7.29 (dd, 2H, Aryl-H), 7.45 (d, 2H, Aryl-H), 7.58 (s, 1H, thiazole-H), 7.67 (d, 2H, pyridine-H), 8.64 (d, 2H, pyridine-H), 11.49 (s, 1H, NH).

EXAMPLE 11

Preparation of N-2-nicotinoyl-4,5,6,7-tetrahydrobenzo[$_d$]thiazol-2-amine (labeled as TJ-M201057)

The reaction process and treatment were the same as that in Example 10. A light yellow powder was obtained. A yield thereof was 34%, a melting point thereof was 189-192° C. UV (MeOH, λmax/nm): 212.4; IR (KBrσ/cm$^{-1}$): 3421 (s, v$_{N—H}$), 2930 (m, pyridine ring v$_{—HC=}$), 1641 (s, v$_{C=O}$), 1542 (s, thiazole ring v$_{—C=N}$); $^1$H-NMR (CDCl$_3$, 300 MHz, δ/ppm): 1.63 (m, 4H, CH$_2$), 2.58 (m, 4H, CH$_2$), 7.38 (s, 1H, pyridine-H), 8.24 (s, 1H, pyridine-H), 8.68 (s, 1H, pyridine-H), 8.77 (s, 1H, pyridine-H), 9.19 (s, 1H, —NH—).

EXAMPLE 12

Preparation of ((1H-indol-3-yl)methylene)-4-(2,4-diethoxy-phenyl)-thiazol-2-amine (labeled as TJ-M201061)

1.6 g (0.006 mol) of 4-(2,4-diethoxy-phenyl)-2-aminothiazole (c) and 0.9 g (0.006 mol) of indole-3-carboxaldehyde were mixed and dissolved in a 20 mL of anhydrous ethanol to form a solution. 3 drops of hexahydropyridine were added to the solution as a catalyst. The solution was stirred for reaction in the presence of microwave irradiation at a power of 65 W for 1 min, then the power of the microwave was controlled at 130 W for allow the solution to continue reaction for 1 h to obtain a yellow turbid solution. The yellow turbid solution was suction filtrated. A filter cake was washed by water for 2 or 3 times, and was desiccated in vacuum to obtain 2.2 g of a yellow powder. A yield thereof was 93.8%, a melting point thereof was 218-220° C. IR (KBr)/cm$^{-1}$ 3224, 3113, 1523.72, 1486.64. $^1$H-NMR (DMSO-d6) 1.34 (t, J=6.6 Hz, 3H), 1.48 (t, J=6.6 Hz, 3H), 4.01 (q, J=6.6 Hz, 2H), 4.10 (q, J=6.6 Hz, 2H), 6.47 (d, J=2.4 Hz, 1H), 6.48 (dd, J=7.2 Hz and J=2.4 Hz, 1H), 7.16-7.21 (m, 2H), 7.58 (d, J=7.2 Hz, 1H), 7.68 (d, J=3.6 Hz, 1H), 7.85 (d, J=7.2 Hz, 1H), 8.15 (d, J=7.2 Hz, 1H), 8.38 (d, J=3.6 Hz, 1H), 9.10 (s, 1H), 11.64 (s, 1H). $^{13}$C-NMR (DMSO-d6) 171.27, 164.70, 158.31, 156.20, 147.64, 136.52, 134.14, 129.73, 123.84, 122.37, 121.13, 120.62, 115.17, 113.67, 110.96, 104.21, 98.40, 62.74, 62.27, 13.77, 13.69. MS (ESI positive ion) m/z: 392.2 (M+1).

EXAMPLE 13

Preparation of (((1H-indol-3-yl)methylene)-4-(naphthalen-1-yl) thiazol-2-amine (labeled as TJ-M201064)

0.7 g (0.003 mol) of 4-(naphthalen-1-yl)-2-aminothiazole and 0.4 g (0.003 mol) of indole-3-carboxaldehyde were mixed and dissolved in a 25 mL of anhydrous ethanol to form a solution. 3 drops of hexahydropyridine were added to the solution as a catalyst. The solution was stirred for reaction in the presence of microwave irradiation at a power of 65 W for 1 min, then the power of the microwave was controlled at 130 W for allow the solution to continue reaction for 1.3 h to obtain a yellow turbid solution. The yellow turbid solution was suction filtrated. A filter cake was washed by water for 2 or 3 times, and was desiccated in vacuum to obtain 1.0 g of a yellow powder. A yield thereof was 94.4%, a melting point thereof was 239-241° C. IR (KBr, σ/cm$^{-1}$): 3102.94 (s, thiazole ring v$_{HC=}$), 3056.71 (w, phenyl ring v$_{=C—H}$), 1598.24 (s, v$_{C=C}$), 1520.61 (m, Schiff basev$_{C=N}$), 1497.64 (m, thiazolev$_{C=N}$), 778.05, 740.33 (δ naphthyl ring bend), 740.33 (δ phenyl ring bend); $^1$H-NMR (DMSO, 300 MHz, δ/ppm): 12.13 (s, 1H, NH), 9.21 (s, 1H, CH=N), 8.33-8.37 (m, 2H, naphthyl-H), 8.27 (s, 1H, indyl-H), 7.95-7.98 (m, 2H, naphthyl-H), 7.73, 7.72 (d, 1H, indyl-H), 7.64 (s, 1H, thiazole-H), 7.54-7.57 (m, 2H, naphthyl-H), 7.54, 7.53 (d, 1H, indyl-H), 7.51, 7.50 (d, 1H, naphthyl-H), 7.22-7.27 (m, 2H, indyl-H); $^{13}$C-NMR (DMSO, 300 MHz, 6/ppm): 174.53 (C10), 159.57 (C9), 152.74 (C11), 138.28 (C13), 138.16 (C8), 134.16 (C17), 133.60 (C22), 131.39 (C1), 129.21 (C16), 128.96 (C18), 127.96 (C21), 127.12 (C19), 126.66 (C20), 126.52 (C15), 126.15 (C3), 125.26 (C14), 124.18 (C5), 122.65 (C6), 122.52 (C4), 115.63 (C7), 114.95 (C12), 113.13 (C2).

EXAMPLE 14

Inhibition of TJ-M2010 type 2-aminothiazole derivative on acetylcholine esterase Inhibition effect of some TJ-M2010 type 2-aminothiazole derivative on acetylcholine esterase was tested using Ellman method. Acetylcholine esterase was originated from SD rats. Two SD rats having a weight of between 160 and 180 g were provided. Hippocampus was collected from rats' brains at a low temperature. 2 mL of a lysis buffer was used to lysis and homogenate. A resulting mixture was centrifuged at a rotational speed of 3000 r/min for 15 min, and a supernatant was obtained and preserved at a temperature of −20° C. Measured by BCA method, a content of a homogenate protein was 11.383 mg/mL (absorbance A=0.428), standard solution 10 mg/mL (absorbance A=0.376). TJ-M201018 (1), TJ-M201005 (2), TJ-M201041 (3), TJ-M201021 (4), TJ-M201064 (5), and TJ-M201057 (6) were tested. 1% of DMSO enzyme solution was employed as a blank control, and tacrine was employed as a positive control. Results were shown in FIG. 1.

From the results, it was known that TJ-M2010 type 2-aminothiazole derivative had a certain inhibition effect on AchE, and an inhibition effect thereof was comparative to that of Tacrine.

EXAMPLE 15

Inhibition of the Aminothiazole Derivatives Provided in the Invention on PARP-1

Universal chromogenic method kit (R&D Catalog Number 4677-096-K) was employed. The principle was as follows: a bottom of a 96-well plate was coated with histone. The histone was a substrate in a PARP-1 catalytic reaction. To each well, PARP-1 enzyme, biotin-labeled NAD+, activator Nicked DNA, and various inhibitors were added, respectively. PARP-1 was activated by activator Nicked DNA. The activated PARP-1 catalyzed PAR to connect with the histone to form an ARP-1-PAR-histone compound fixed on the bottom. The protein complex was connected to a chromogenic HRP (horseradish peroxidase). After a proper time of reaction, the reaction solution was discarded. After been washed, substrate TACS was added. The substrate TACS can be catalyzed by HRP. A microplate reader was employed to measure reading at 630 nm. The reaction can be finished by 0.2 N hydrochloric acid, and readings were collected at 450 nm.

Figure 2:
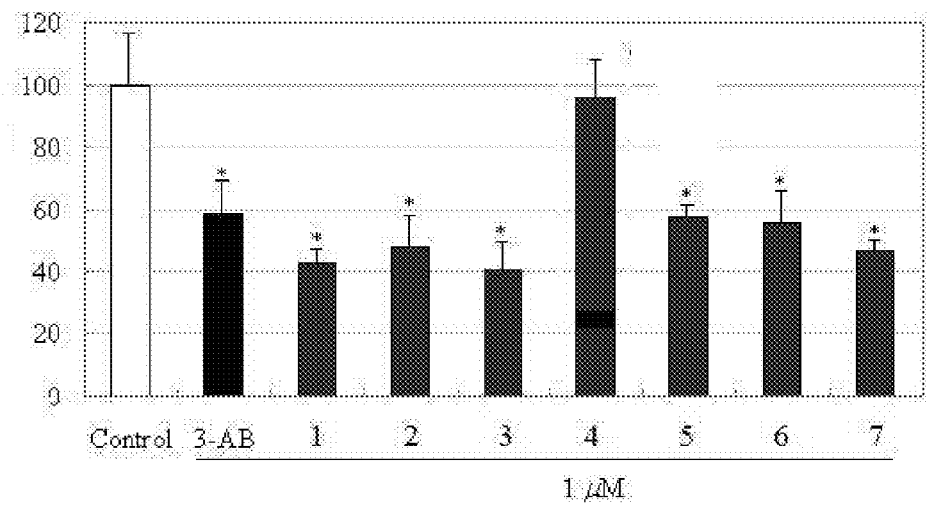
FIG. 2 shows inhibition effect of an aminothiazole derivative in accordance with one embodiment of the invention on PARP-1.

Within a concentration of between 2 M and 10 mM, the typical PARP-1 inhibitor 3-AB had an inhibition effect on the PARP-1, so that it was used as the positive control. TJ-M201018 (1), TJ-M201005 (2), TJ-M201041 (3), TJ-M201021 (4), TJ-M201064 (5), TJ-M201057 (6), and TJ-M201061 (7) were tested. Results were shown in FIG. 2, it was known that TJ-M201018 (1), TJ-M201005 (2), TJ-M201041 (3) have an inhibition rate on the PARP-1 of exceeding 50% when concentration thereof were 1 M.

EXAMPLE 16

Figure 3:
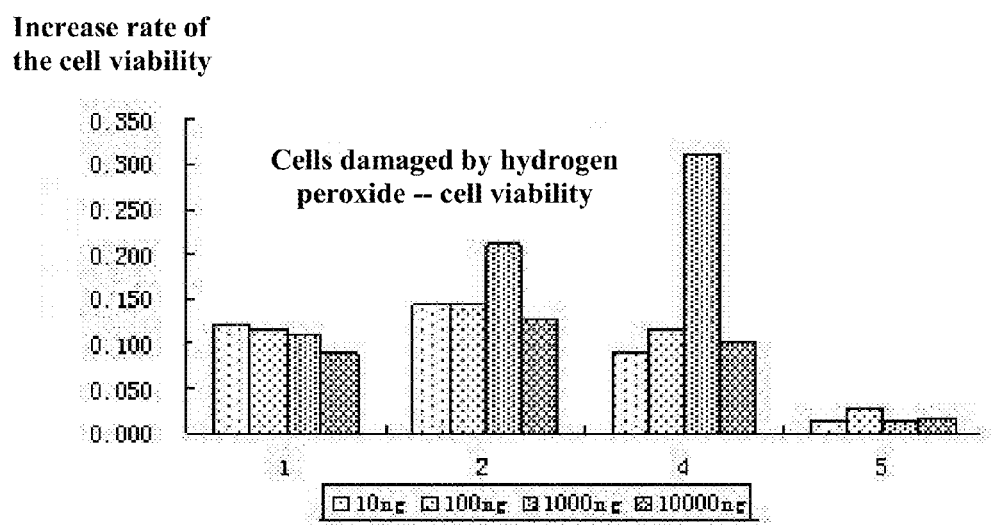
FIG. 3 shows cytoprotective ability of an aminothiazole derivative in accordance with one embodiment of the invention against hydrogen peroxide (increase rate of the cell viability)

Protection of Aminothiazole Derivatives Provided in the Invention Against Neuronal Apoptosis Induced by Hydrogen Peroxide Dopaminergic neuroblastoma tumor cells SH-SY5Y from human body were employed as experiment cells. $H_2O_2$ having a concentration of 1000 μM/L was used to treat SH-SY5Y cells for 12 h. Cell viability was approximately 50%, and a hydrogen peroxide damage model was determined MTT method was used to test the protection of TJ-M201018 (1), TJ-M201005 (2), TJ-M201041 (3), TJ-M201021 (4), and TJ-M201064 (5) on the cells damaged by hydrogen peroxide; results were shown in FIG. 3.

It was known from the results that TJ-M201021 (4) had a certain protection on the SH-SY5Y cells against hydrogen peroxide having a concentration of 1 μM; cell viability therein was 30%.

EXAMPLE 17

Figure 4:
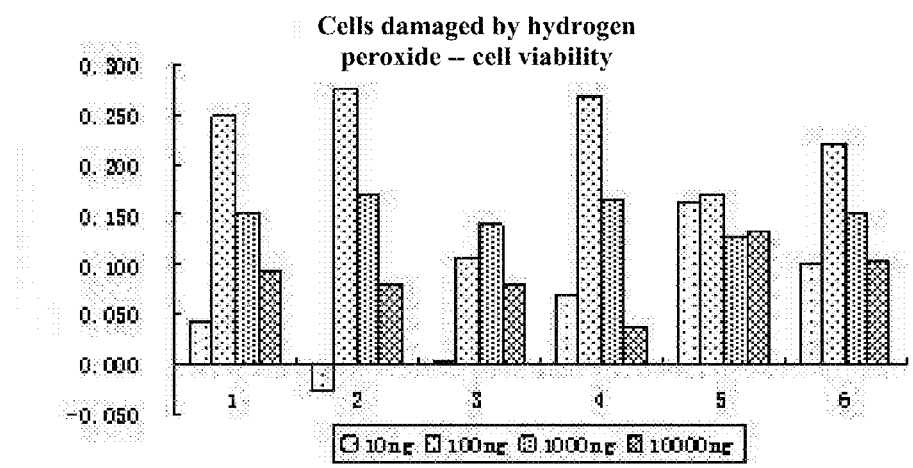
FIG. 4 shows cytoprotective ability of an aminothiazole derivative in accordance with one embodiment of the invention against cobalt chloride (increase rate of the cell viability)

Use of Aminothiazole Derivatives Provided in the Invention Against Neuronal Apoptosis Resulting from Cobalt Chloride-Induced Hypoxic Injury Dopaminergic neuroblastoma tumor cells SH-SY5Y from human body were employed as experiment cells. Cobalt chloride having a concentration of 600 μM/L was used to treat SH-SY5Y cells for 24 h. Cell viability was approximately 50%, and a cobalt chloride damage model was determined MTT method was used to test the protection of TJ-M201018 (1), TJ-M201005 (2), TJ-M201041 (3), TJ-M201021 (4), and TJ-M201064 (5) of different concentrations on the cells damaged by cobalt chloride; results were shown in FIG. 4.

Figure 5:
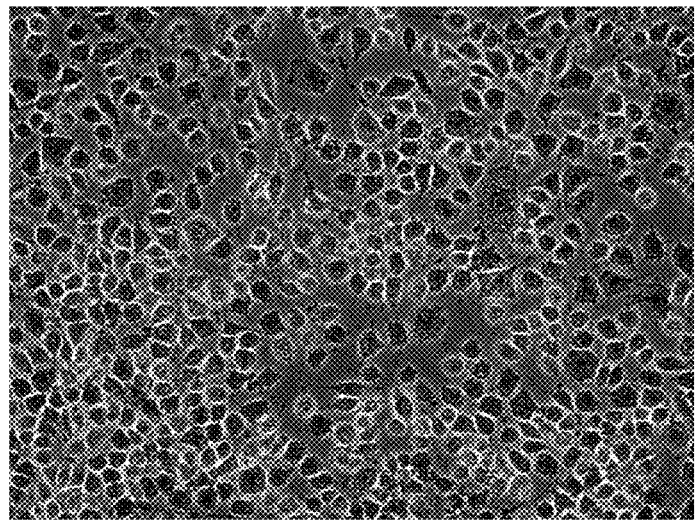
FIG. 5 shows SH-SY5Y cells after being damaged by cobalt chloride.
Figure 6:
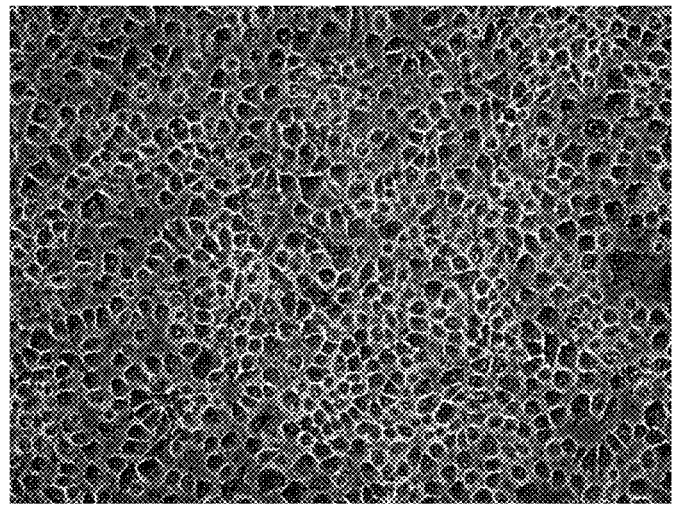
FIG. 6 shows cobalt chloride-damaged SH-SY5Y cells being added with an aminothiazole derivative in accordance with one embodiment of the invention.

It was known from the results that the aminothiazole derivatives have good protection on the cell against hypoxic injuries caused by cobalt chloride. Observed under the microscope, cells after being damaged (FIG. 5) had unclear edges, and the number of the cells was decreased. In samples added with TJ-M201021 (4), as shown in FIG. 6, a large number of cells existed and had clear edges. The growth of the cells was good.

EXAMPLE 18

Use of Aminothiazole Derivatives Provided in the Invention in Treatment of Autoimmune Diseases In vitro experiment—results from flow cytometry proved that MyD88 was capable of inhibiting the mature of DC cells for treating autoimmune diseases.

In vitro experiment comprised the following steps:

1. The aminothiazole derivative labeled as TJ-M201021 (Example 8) was applied to bone marrow cell from BALB/c mice. Membrane of the marrow cells was broken. The marrow cells were then cultured in a RPMI1640 medium (added with GM-CSF10 ng/mL, IL-4 10 ng/mL); a concentration of the marrow cells was controlled at 2×106/mL.

2. After being cultured for 48 h, suspended cells were removed; after six days of culture, suspended cells and semi-adherent cells were collected.

3. DC cells were added with 50 mM of TJ-M201021 and cultured for 1 h. The medium was then added with a supernatant of necrotic myocardium, LPS (200 ng/mL), Poly I: C (20 mg/mL), and CpG (10 mg/mL) and cultured for 12 h.

Figure 7:
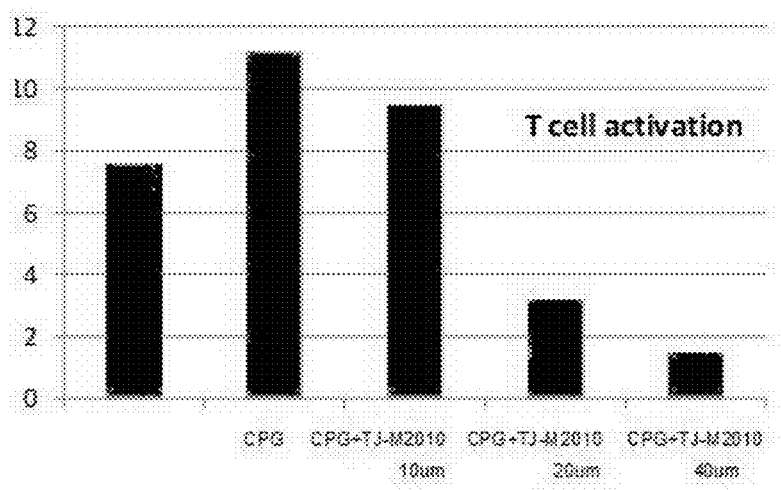
FIGS. 7-10 show increase of co-stimulatory molecules CD80 caused by inhibition of an aminothiazole derivative on LPS and CpG.
Figure 8:
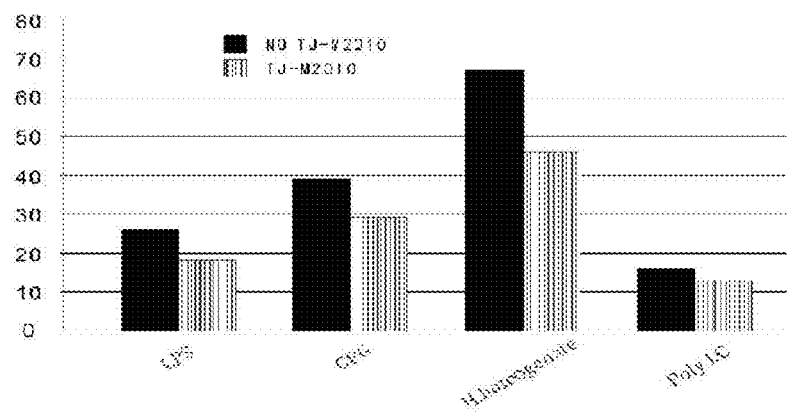
Figure 9:
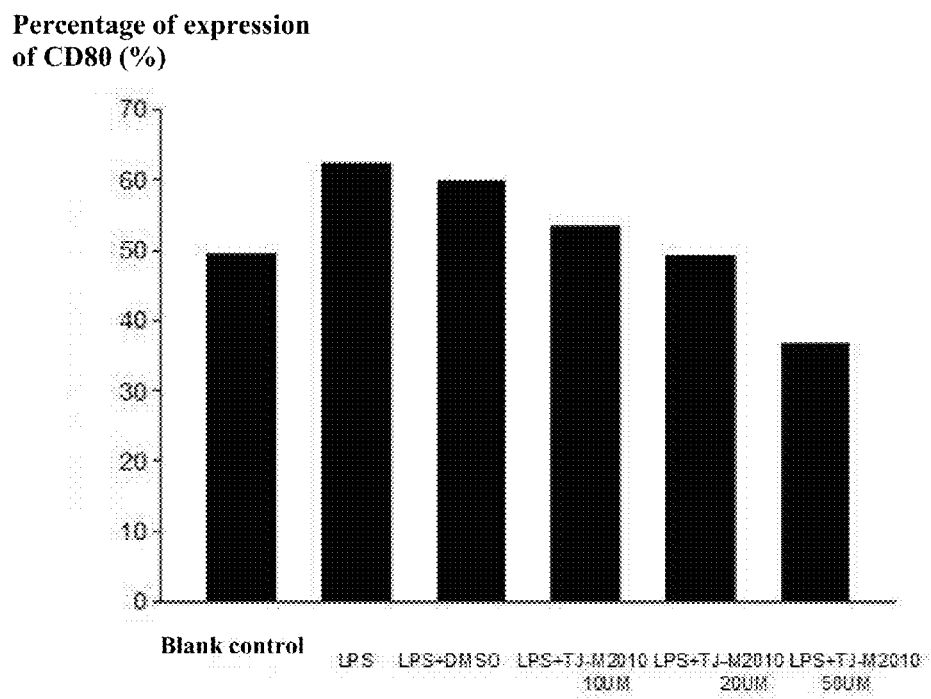
Figure 10:
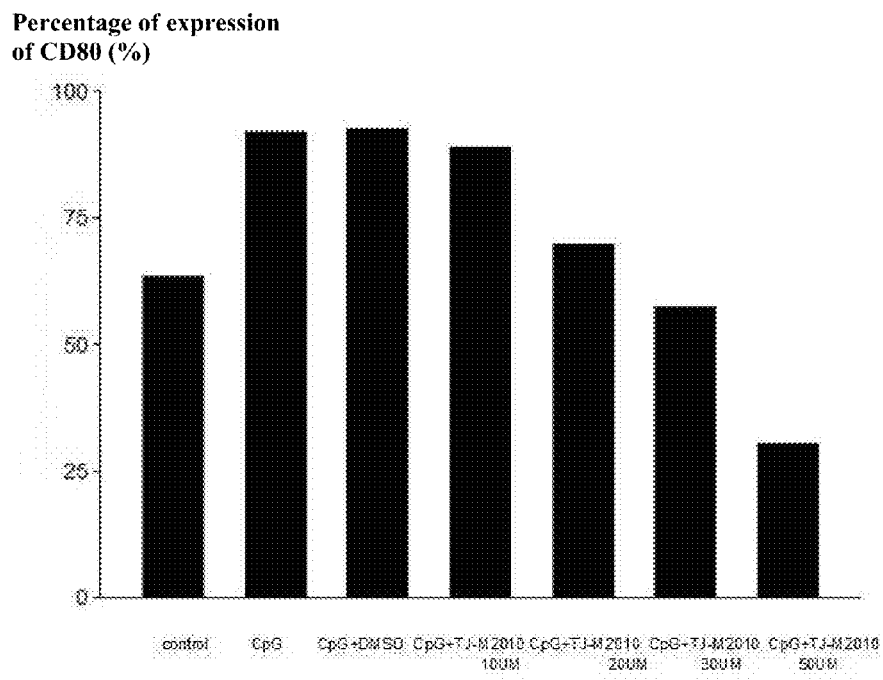

4. Flow antibodies FITC-labeled anti-CD80, CD86 were added for testing. TJ-M201021 inhibited the increase of the costimulatory molecules CD80 in RAW264.7 cells cause by TLR stimuli (LPS, CpG). Thus, TJ-M201021 effectively blocked the TLR signaling pathway, thereby inhibiting the immune response of the cell, as shown in FIGS. 7, 8.

Raw264.7: 48-well plate, cells number of 9*105/well. Each well was added with 1 mL of culture system. Different concentrations of TJ-M201021 were added, and cells were pre-incubated for 2 h. CPG was then added. A final concentration was 40 ug/mL. Cells were incubated for 12 h at a temperature of 37° C. in an incubator filled with $CO_2$. Flow antibodies FITC-labeled anti-CD80 and CD86 were added for testing.

DC: 48-well plate, cells number of 1*106/well. Each well was added with 1 mL of culture system. Different concentrations of TJ-M201021 were added, and cells were pre-incubated for 2 h. LPS was then added. A final concentration was 1 ug/mL. Cells were incubated for 12 h at a temperature of 37° C. in an incubator. Flow antibodies FITC-labeled anti-CD80, and CD86 were added for testing.

Thus, aminothiazole derivatives provided in the invention had inhibition on the expression of DC and macrophage cell surface CD80 correlated to a certain range of concentration.

The above test results indicated that MyD88 was capable of lowering the expression of CD80, thereby inhibiting the mature of DC cells. The mature of DC cells had been proved to be one of the critical steps resulting in autoimmune cardiomyopathy, experimental autoimmune inflammatory grapes, 1-type diabetes, multiple sclerosis, and lupus erythematosus. Thus, MyD88 was capable of treating this kind of disease.

In vivo experiment-influence of MyD88−/− and aminothiazole derivatives provided in the invention on Type I diabetes' model building.

In vivo experiment comprised the following steps:
1. Experimental groups: MyD88KONOD mice, MyD88KO/+NOD mice, NOD mice TJ-M201002 (see Example 6) administered.
2. Administered groups: antigen was injected one day before, TJ-M2010 dissolved in 0.5% CMC was respectively intraperitoneally injected on a 0-3th day, a 5th day, a 7th day, a 9th day, a 11th day, a 13th day, a 15th day, 150 mg/kg/d.
3. Each group was injected with mycobacterial antigen and continuously monitored the concentration thereof.
4. Each group was feed for 30 weeks at a clear grade. After that, venous blood in cauda was collected on a non-empty stomach and blood glucose was continuously tested for twice. The diabetes modeling standard was that both blood glucose≥22 mmol/L.

Figure 11:
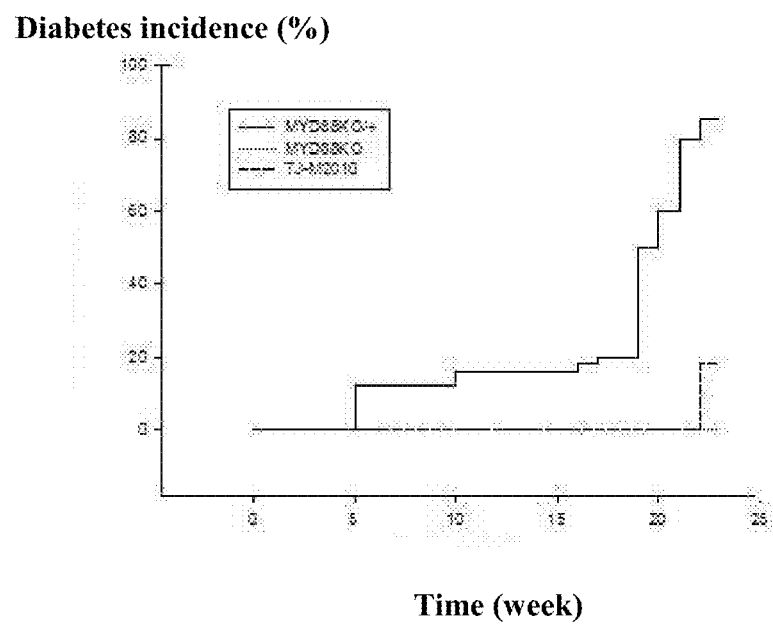
FIG. 11 is a curve chart showing the decrease of diabetes incidence resulting from the treatment of an aminothiazole derivative of the invention.

An incidence curve of type I diabetes was shown in FIG. 11. The results showed that for MyD88KO heterozygous group, the incidence of the type I diabetes increased with the increase of the time. The MyD88KO homozygous group had no incidence of the type I diabetes. The incidence of the type I diabetes of Aminothiazole derivatives group was equivalent to that of the MyD88KO homozygous group. Thus, MyD88 pathway had a close relationship with type I diabetes. To block of the MyD88 pathway was to decrease the incidence of the diabetes, so that the small molecule MyD88 inhibitor TJ-M2010 was effective in treatment of type I diabetes.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:
1. 3-(4-(4-methoxyphenyl)piperazin-1-yl)-N-(4-phenyl-thiazol-2-yl)-propionamide.

* * * * *